(12) United States Patent
Frost et al.

(10) Patent No.: US 7,002,047 B2
(45) Date of Patent: *Feb. 21, 2006

(54) BIOCATALYTIC SYNTHESIS OF QUINIC ACID AND CONVERSION TO HYDROQUINONE

(75) Inventors: John W. Frost, Okemos, MI (US); Karen M. Frost, Okemos, MI (US)

(73) Assignee: Board of Trustees Operating Michigan State University, East Lansing, MI (US)

( * ) Notice: Subject to any disclaimer, the term of this patent is extended or adjusted under 35 U.S.C. 154(b) by 17 days.

This patent is subject to a terminal disclaimer.

(21) Appl. No.: 10/435,242

(22) Filed: May 9, 2003

(65) Prior Publication Data

US 2003/0203460 A1 Oct. 30, 2003

Related U.S. Application Data

(63) Continuation of application No. 09/427,394, filed on Oct. 25, 1999, now Pat. No. 6,600,077, which is a continuation-in-part of application No. 09/240,441, filed on Jan. 29, 1999, now abandoned.

(51) Int. Cl.
*C07C 37/68* (2006.01)
*C07C 45/00* (2006.01)
*C07C 39/00* (2006.01)
*C12P 7/66* (2006.01)
*C12P 7/02* (2006.01)

(52) U.S. Cl. ........................ 568/749; 568/322; 568/716; 568/811; 552/291; 552/293; 435/133; 435/155; 435/156

(58) Field of Classification Search ................ 568/749, 568/322, 716, 811; 435/133, 155, 156; 552/291, 552/293

See application file for complete search history.

(56) References Cited

U.S. PATENT DOCUMENTS

| 5,798,236 A | 8/1998 | Frost et al. |
| 6,600,077 B1 | 7/2003 | Frost et al. |
| 2002/0142409 A1 | 10/2002 | Frost et al. |

OTHER PUBLICATIONS

Barco, A. et al., *Tetrahedron Asymmetry*, 8:3515 (1997).
Brown, K.D. et al., *Biochem. Biophys. Acta*, 428:550 (1976).
Dell, K. et al., *J. Am. Chem. Soc.*, 115:1158 (1993).
Draths, K. et al., *J. Am. Chem. Soc.*, 114:9725 (1992).
Draths, K. et al., *J. Am. Chem. Soc.*, 117:2395 (1995).
Falck, J. et al., *J. Org. Chem.*, 54:5851 (1989).
Mitsuhashi, S. et al., *Biochim. Biophys. Acta*, 15:268 (1954).
Ran, N. et al., *J. Am. Chem. Soc.*, 123:10927 (2001).
Rao, A. et al., *Tetrahedron Lett.*, 32:547 (1991).
White, J. et al., *J. Am. Chem. Soc.*, 111:8970 (1989).
Woskresensky, A., *Justus Liebig's Ann. Pharm.*, 27:257 (1838).

*Primary Examiner*—Rebecca E. Prouty
*Assistant Examiner*—Delia M. Ramirez
(74) *Attorney, Agent, or Firm*—Harness, Dickey & Pierce, P.L.C.

(57) ABSTRACT

A bioengineered synthesis scheme for the production of quinic acid from a carbon source is provided. Methods of producing quinic acid from a carbon source based on the synthesis scheme as well as conversion of quinic acid to hydroquinone are also provided.

13 Claims, 4 Drawing Sheets

(a) NaOCl, H$_2$SO$_4$, rt, 81%; (b) reflux, 72%.

(a) NaOCl, H$_2$SO$_4$, rt, 41%; (b) acetone, TsOH, 0°C, 59%; (c) Ac$_2$O, (*i*-Pr)$_2$NEt, DMAP, CH$_2$Cl$_2$, 0°C, 91%; (d) CF$_3$CO$_2$H/H$_2$O (2:1, v/v), 0°C, 43%; (e) (i) CH$_3$OH, Dowex 50 (H$^+$), reflux; (ii) 2,3-butanedione, CH(OCH$_3$)$_3$, CH$_3$OH, CSA, reflux, 79%; (f) LiAlH$_4$, THF, 0°C, rt, 93%; (g) NaIO$_4$, phosphate buffer (pH 7), 0°C, rt, 72%; (h) Ac$_2$O, (*i*-Pr)$_2$NEt, DMAP, CH$_2$Cl$_2$, 0°C, 100%; (i) CF$_3$CO$_2$H/CH$_2$Cl$_2$/H$_2$O (9:1:1, v/v/v), 0°C, 75%.

BIOCATALYTIC SYNTHESIS OF QUINIC ACID AND CONVERSION TO HYDROQUINONE

RELATED APPLICATIONS

The present invention is a continuation of U.S. Ser. No. 09/427,394, filed Oct. 25, 1999, now U.S. Pat. No. 6,600,077, which is a continuation-in-part of U.S. Ser. No. 09/240,441, filed Jan. 29, 1999, now abandoned, which is hereby expressly incorporated by reference.

SPONSORSHIP

Work on this invention was sponsored in part by the United States Department Of Agriculture Grant No. 95-37500-1930 and the National Science Foundation Grant No. CHE963368 amendment 002. The Government may have certain rights in the invention.

FIELD OF THE INVENTION

The present invention is related to the production of quinic acid and more specifically, to methods of producing quinic acid and derivatives of quinic acid from the bioconversion of a carbon source.

BACKGROUND OF THE INVENTION

Quinic acid is an attractive chiral synthon with its highly functionalized, six-membered carbocyclic ring and multiple asymmetric centers. Both hydroquinone and benzoquinone, which are industrially important organic compounds, can be derived by magnesium (IV) dioxide oxidation of quinic acid. Woskrensensky, A., *Justus Liebigs Ann. Chem.* 27:257 (1838). Quinic acid is an important molecule utilized as an enantiomerically pure starting material for the synthesis of various molecules, many of which are biologically important. For example, quinic acid is a useful starting material for the synthesis of FK-506, an immune suppressive agent useful in preventing organ transplant rejection. Rao, A. V. R. et al., *Tetrahedron Lett.* 32:547 (1990). Additionally, quinic acid has been utilized in the synthesis of the neuraminidase inhibitor GS401 and GS4104, an important new pharmaceutical for the treatment of influenza. Barco, A. et al., *Tetrahedron Asymmetry* 8:3515 (1997). It is also utilized as a convenient source for the synthesis of many natural products that are otherwise difficult to obtain (e.g., mycosporin and D-myo-inositol-1,4,5-triphosphate. White et al., *J. Am. Chem Soc.* 111(24):8970 (1989); Falck et al., *J. Org. Chem.* 54(25):5851 (1989), respectively. In addition, quinic acid is utilized as a food additive, resolving agent and is being used experimentally in optical materials.

Quinic acid has previously been isolated from natural sources (e.g., cinchona bark, tobacco leaves, carrot leaves, etc.). However, the cost of isolating quinic acid from such sources precludes its use as an economically viable starting material. Quinic acid has been synthesized chemically, but such synthesis utilizes organic solvents, highly reactive reagents and hazardous waste and as such is not environmentally desirable. Therefore, there is a need for a cost effective, environmentally desirable method for the synthesis of quinic acid.

U.S. Pat. No. 5,798,236 describes a method for quinic acid production that uses a heterologous biocatalyst in which expression of quinate dehydrogenase from the *Klebsiella pneumoniae* qad gene in *Escherichia coli* results in conversion of 3-dehydroquinic acid (DHQ) into quinic acid. Fermentation of this organism, *E. coli* AB2848aroD/pKD136/pTW8090A (ATCC 69086) produces a mixture of quinic acid, DHQ, and 3-dehydroshikimic acid (DHS). While the relative molar ratio of the three products varies with fermentation conditions, the molar ratio of quinic acid to DHQ and to DHS fails to exceed 2:1:1. The appearance of DHQ as a major byproduct is likely due to product inhibition of quinate dehydrogenase by quinic acid. Alternatively, the specific activity of quinate dehydrogenase may be low due to poor expression of the *Klebsiella* gene in *E. coli* or due to instability of the plasmid carrying the qad locus. The appearance of DHS may represent some instability in the host organism itself.

Hydroquinone is a pseudocommodity chemical used in photographic developers, polymerization inhibitors and antioxidants. Annual production of hydroquinones is in the 40,000–50,000 ton range. Krumenacher, L. et al. Hydroquinone is currently synthesized via hydroperoxidation of p-diisopropylbenzene as well as oxidation of aniline or hydroxylation of phenol with hydrogen peroxide. U.S. Pat. No. 5,798,236; Krumenacher, L. et al. Aniline, phenol, or p-diisopropylbenzene are produced from carcinogenic benzene starting material, which is obtained from nonrenewable fossil fuel feedstocks. Methods have also been described for converting quinic acid to hydroquinone. U.S. Pat. No. 5,798, 236. The quinic acid is over oxidized to benzoquinone via hydroquinone, and the benzoquinone is then converted back to hydroquinone.

It would thus be desirable to provide a method for the production of quinic acid, which method utilizes a carbon source as a starting material which can be derived from a renewable resource. It would also be desirable to provide a method for the production of quinic acid in which quinic acid is the major product at high concentrations compared to by-products such as DHQ and DHS.

It would also be desirable to provide a method for the production of hydroquinone from quinic acid. It would be further desirable for the method to be inexpensive and utilize non-toxic and non-carcinogenic reactants. It would also be desirable for such a method to produce high-purity hydroquinone in good yields without overoxidation of quinic acid to benzoquinone.

SUMMARY OF THE INVENTION

A bioengineered synthesis scheme for production of quinic acid from a carbon source is provided. In one embodiment, the bioconversion methods of the present invention comprise the microbe-catalyzed conversion of a carbon source to quinic acid. As shown in the synthesis scheme of FIG. 1, the microbe-catalyzed conversion step of the present invention requires three enzymes which are provided by a recombinant microbe. In a preferred embodiment, the recombinant microbe is *Escherichia coli* designed to cause reduction of 3-dehydroquinate to quinic acid instead of dehydration of 3-dehydroquinate to dehydroshikimate.

The biocatalytic synthesis of quinic acid provided herein is environmentally benign, economically attractive, and utilizes abundant renewable sources as a starting material.

Also provided are methods for the conversion of quinic acid to hydroquinone. In one embodiment, quinic acid is initially oxidized to 3,4,5-trihydroxycyclohexanone 1 (FIG. 4). In a preferred embodiment, quinic acid is oxidized by reaction with hyperchloric acid. Subsequent heating of 3,4, 5-trihydroxycyclohexanone 1 yields hydroquinone.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

Figure 1:
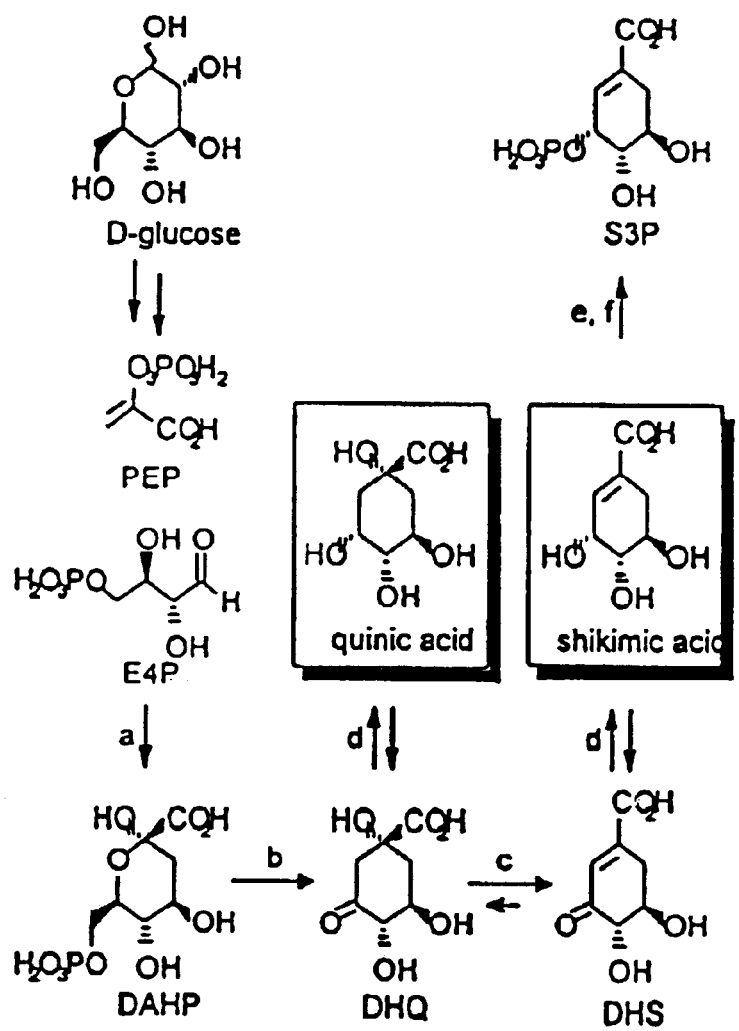
FIG. 1 is a schematic illustrating the bioengineered synthesis scheme of the present invention for producing quinic acid.

A bioengineered synthesis scheme for the production of quinic acid from a carbon source is provided herein. Methods of producing quinic acid from a carbon source based on the synthesis scheme of FIG. 1 are also provided. Methods for converting quinic acid to hydroquinone are provided as well.

In one embodiment, a method is provided wherein the carbon source is converted to quinic acid by a recombinant microbe. Manipulation of the common aromatic amino acid biosynthetic pathway of the microbe results in a significant production of quinic acid when the recombinant microbe is cultured in the presence of a carbon source. The carbon source is converted to 3-deoxy-D-arabino-heptulosonate-7-phosphate (DAHP) which is subsequently converted by 3-dehydroquinate synthase to 3-dehydroquinate (DHQ) which is then reduced to quinic acid by shikimate dehydrogenase (d, FIG. 1). The conversion of 3-dehydroquinate to quinic acid was discovered when studying the production of shikimic acid in $E.$ $coli$ SP1.1/pKD12.112 from a carbon source as described in Specific Example 1. Quinic acid biosynthesis is surprising given the absence in $E.$ $coli$ of quinate dehydrogenase which catalyzes the interconversion of 3-dehydroquinate and quinic acid. This unprecedented activity of shikimate dehydrogenase in the interconversion of 3-dehydroquinate and quinic acid has been confirmed by incubating 3-dehydroquinate with purified shikimate dehydrogenase.

Quinic acid biosynthesis, while widespread in plants, has only been observed in a single microbe, $E.$ $coli$ AB2848aroD/pKD136/pTW8090A. Draths, K. M. et al., $J.$ $Am.$ $Chem.$ $Soc.$ 114:9725 (1992); and U.S. Pat. No. 5,798, 236. This heterologous construct expresses quinate dehydrogenase encoded by the qad locus isolated from $Klebsiella$ $pneumoniae$. Mitsuhashi, S. et al., $Biochim.$ $Biophys.$ $Acta$ 15:268 (1954). Quinate dehydrogenase-catalyzed oxidation of quinic acid is driven by catabolic consumption of the resulting 3-dehydroquinic acid via the β-ketoadipate pathway in $K.$ $pneumoniae$ and other microbes. Reduction of 3-dehydroquinic acid by quinate dehydrogenase dominates in $E.$ $coli$ AB2848aroD/pKD136/pTW8090A because of the absence of 3-dehydroquinic acid catabolism. Quinic acid synthesis in $E.$ $coli$ SP1.1/pKD12.112 thus implicates the existence of an oxidoreductase which reduces 3-dehydroquinic acid.

The bioconversion methods of the present invention are carried out under conditions of time, temperature, pH, nutrient type and concentration, aeration conditions, and controlled glucose concentrations, to provide maximal conversion of the carbon source to quinic acid. As described in detail in Specific Example 2, in a preferred embodiment, a fed-batch fermentor is used to convert the carbon source to quinic acid, followed by isolation of the quinic acid from the fermentation broth by ion-exchange chromatography. The batch fermentor process and chromatography methods are also known to those skilled in the art.

As used herein, the phrase "carbon source" is meant to include biomass derived carbon sources including, but not limited to, xylose, arabinose, glycerol, glucose and the intermediates in the Krebs cycle (e.g., dicarboxylic acids), either alone or in combination. In a preferred embodiment, the carbon source is glucose. The carbon source may be derived from renewable resources such as, without limitation, corn, sugar, beets and sugar cane.

In one embodiment, the recombinant microbe employed in the methods of the present invention is $E.$ $coli$. In a preferred embodiment, the $E.$ $coli$ comprises a mutated aroD locus and an aroB cassette inserted into the serA locus. This recombinant $E.$ $coli$, designated QP1.1, may further comprise a plasmid carrying aroF$^{FBR}$, aroE and serA gene inserts. The blocking or impeding of aroD-encoded 3-dehydroquinate dehydratase (c, FIG. 1) results in the accumulation of 3-dehydroquinate which is subsequently converted to quinic acid. It will be appreciated, however, that the aroD locus mutation is not essential and is employed to further provide 3-dehydroquinate and to decrease the formation of 3-dehydroshikimate acid. The aroB gene insert encodes 3-dehydroquinate synthase (b, FIG. 1), increasing the production of 3-dehydroquinate. The 3-dehydroquinate is converted into quinic acid by plasmid-localized aroE-encoded shikimate dehydrogenase (d, FIG. 1).

In a preferred embodiment, the recombinant $E.$ $coli$ comprises plasmid pKD12.112 carrying aroF$^{FBR}$, serA and aroE gene inserts. The aroF$^{FBR}$ gene insert encodes a mutant 3-deoxy-D-arabino-heptulosonate-7-phosphate synthase isozyme (a, FIG. 1) insensitive to feedback inhibition by aromatic amino acids or other aromatic molecules which increases carbon flow into the common aromatic amino acid biosynthetic pathway. Due to a mutation in the $E.$ $coli$ genomic serA locus required for L-serine biosynthesis, growth in minimal salts medium and plasmid maintenance follows from expression of plasmid-localized serA. The serA insert thus allows microbial growth in minimal salts medium, distinguishing the microbes containing the plasmid from non-plasmid containing microbes. The aroE gene insert encodes a shildmate dehydrogenase, increasing the production of quinic acid. Preferably, the aroE gene is from $E.$ $coli$. More preferably, all the inserted genes are from $E.$ $coli$, producing a homogenous recombinant $E.$ $coli$.

In another embodiment, the aroF$^{FBR}$, serA and/or aroE genes are inserted directly into the $E.$ $coli$ genome along with aroB. Such a recombinant $E.$ $coli$ would not require a plasmid to produce significant amounts of quinic acid.

The above-described preferred recombinant microbe of the present invention, $E.$ $coli$ QP1.1/pKD12.112, has been deposited with the American Type Culture Collection (ATCC), 12301 Parklawn Drive, Rockville, Md. 20582, under the terms of the Budapest Treaty, and has been accorded the ATCC designation number 98904. The deposit will be maintained in the ATCC depository, which is a public depository, for a period of 30 years, or 5 years after the most recent request, or for the effective life of a patent, whichever is longer, and will be replaced if the deposit becomes depleted or nonviable during that period. Samples of the deposit will become available to the public and all restrictions imposed on access to the deposit will be removed upon grant of a patent on this application.

The following table sets forth the three enzymes required for the conversion of glucose to quinic acid, the genes encoding same and the origin of the genes in the exemplary recombinant microbes of the present invention.

TABLE 1

| Enzyme[†] | Gene (origin) |
| --- | --- |
| a) 3-deoxy-D-arabino-heptulosonic acid 7-phosphate synthase | aroF$^{FBR}$ (plasmid) |
| b) 3-dehydroquinate synthase | aroB (additional copy inserted into genome) |
| d) 3-dehydroshikimate dehydrogenase | aroE (plasmid) |

[†]Enzymes a), b) and d) correspond to a, b and d of FIG. 1.

Although *E. coli* is specifically described herein as the microbe for carrying out the methods of the present invention, it will be appreciated that any microorganism such as the common types cited in the literature and known to those skilled in the art, may be employed, provided the microorganism can be altered to effect the desired conversion (e.g., carbon source to quinic acid, carbon source to 3-dehydroquinate, 3-dehydroquinate to quinic acid, etc.) Thus, it is envisaged that many types of fungi, bacteria and yeasts will work in the methods of the present invention. Such microorganisms may be developed, for example, through selection, mutation, and/or genetic transformation processes with the characteristic and necessary capability of converting one constituent of the synthesis scheme of the present invention to another. Methods for such development are well known to the skilled practitioner.

In order to carry out the bioconversion methods of the present invention, a solution containing a carbon source is contacted with the recombinant microbe to form a bioconversion mixture which is maintained under appropriate conditions to promote the conversion of the carbon source to the desired constituent, e.g., quinic acid. In a preferred embodiment, the bioconversion mixture is maintained at a temperature of about 30° C. to about 37° C. and a pH of about 6.5 to about 7.5. It is preferred that the bioconversion mixture also contain other substances necessary to promote the viability of the recombinant microbes such as mineral salts, buffers, cofactors, nutrient substances and the like. The bioconversion mixture is preferably maintained in a steady state under glucose limited conditions. In a preferred method the rate of glucose addition is determined by the level of dissolved oxygen concentration. A preferred steady state over the course of fermentation is about 100 to about 200 $\mu$mol glucose or a dissolved oxygen concentration of about 5% to about 35% air saturation. The more general requirements for the maintenance of viability of microorganisms are well known and specific requirements for maintaining the viability of specific microorganisms are also well known as documented in the literature, or are otherwise easily determined by those skilled in the art. The quinic acid may then be recovered from the bioconversion mixture by methods known in the art (e.g., ion-exchange chromatography) and further purified by recrystallization.

Figure 4:
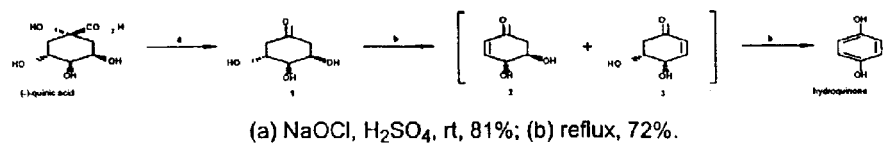
FIG. 4 is a schematic illustrating the synthesis scheme of the present invention for converting quinic acid to hydroquinone.

Novel methods for converting quinic acid to hydroquinone are also provided. In one embodiment, a method is provided wherein oxidation of quinic acid and heating of the oxidation product yields hydroquinone. In one embodiment, quinic acid is oxidized to 3,4,5-trihydroxycyclohexanone which is then heated to produce hydroquinone (FIG. 4).

In one embodiment, the quinic acid is oxidized to 3,4,5-trihydroxycyclohexanone wherein the oxidation is catalyzed by an oxidizing agent. In a preferred embodiment, the oxidizing agent oxidizes quinic acid to 3,4,5,-trihydroxycyclohexanone but not to benzoquinone. Preferably, the oxidizing agent is chosen from the group comprising HOCl, ($H_2SO_4$/NaOCl), $AgNO_3$, $(NH_4)_2Ce(NO_3)_6$, $V_2O_5$, $NH_4VO_3$, and $2KHSO_5.KHSO_4$.(oxone)/NaCl. More preferably, the oxidizing agent is selected from the group comprising HOCl or $AgNO_3$. Most preferably, the HOCl is form in situ by acidifying commercial bleach (NaOCl) in the oxidation reaction mixture. The amount of oxidizing agent required is preferably about 1.0 equivalents relative to quinic acid. Alternatively, the oxidizing agent is present in catalytic amounts of less than about 1.0 equivalents along with at least 1.0 equivalents of a cooxidant. For example, 0.1 equivalents of $AgNO_3$ can effectively oxidize quinic acid in the presence of 1.2 equivalents of $K_2S_2O_8$. While not wishing to be bound by theory, the cooxidant is present to regenerate the oxidizing agent such that only catalytic amounts of the oxidizing agent are required.

In another embodiment, the oxidation reaction is carried out in an aqueous quinic acid solution. In a preferred embodiment, the aqueous quinic acid solution is a purified quinic acid fermentation broth (see Specific Example 3). In an alternate embodiment, the aqueous quinic acid solution is comprised of isolated quinic acid and water. The yield of hydroquinone may be dependent on both the aqueous quinic acid solution and the oxidizing agent. When the reaction was carried out in purified quinic acid fermentation broth, the yield of hydroquinone was 57% (mol/mol) with acidified commercial bleach, 55% (mol/mol) with $(NH_4)_2Ce(NO_3)_6$ and 64% (mol/mol) with $V_2O_5$ as the oxidants. However, when $AgNO_3$ was the oxidant, with $K_2S_2O_8$ as the cooxidant, the yield of hydroquinone from purified quinic acid fermentation broth was only 35% (mol/mol) whereas the yield was increased to 80% (mol/mol) when the aqueous solution comprised purified quinic acid in water.

In a further embodiment, 3,4,5-trihydroxycyclohexanone is dehydrated to produce hydroquinone. In a preferred embodiment, the 3,4,5-trihydroxycyclohexanone is not isolated after the oxidation reaction. After oxidation of quinic acid to 3,4,5-trihydroxycyclohexanone, the reaction mixture is then heated to produce hydroquinone. When HOCl is the oxidizing agent, the oxidation reaction mixture is neutralized before heating. The hydroquinone can then be purified from the reaction mixture by methods known in the art (e.g., extraction, flash chromatography).

In order to more fully demonstrate the advantages arising from the present invention, the following examples are set forth. It is to be understood that the following is by way of example only and is not intended as a limitation on the scope of the invention.

SPECIFIC EXAMPLE 1

Synthesis of Quinic Acid by Shikimate Dehydrogenase

1. Results

Culturing SP1.1/pKD12.112 for 42 h with $K_c$=0.1 resulted in the synthesis of 27.2 g/L of shikimic acid, 12.6 g/L of quinic acid, and 4.4 g/L of 3-dehydroshikimic acid (DHS). DHS accumulation reflected the expected feedback inhibition of shikimate dehydrogenase by shikimic acid. Draths, K. M. et al., *J. Am. Chem. Soc.* 114:9726 (1992); Dell, et al., *J. Am. Chem. Soc.* 115:1158 (1993). By contrast, quinic acid biosynthesis was surprising given the absence in *E. coli* of quinic acid dehydrogenase which catalyzes 3-dehydroquinate and quinic acid interconversion.

Figure 3:
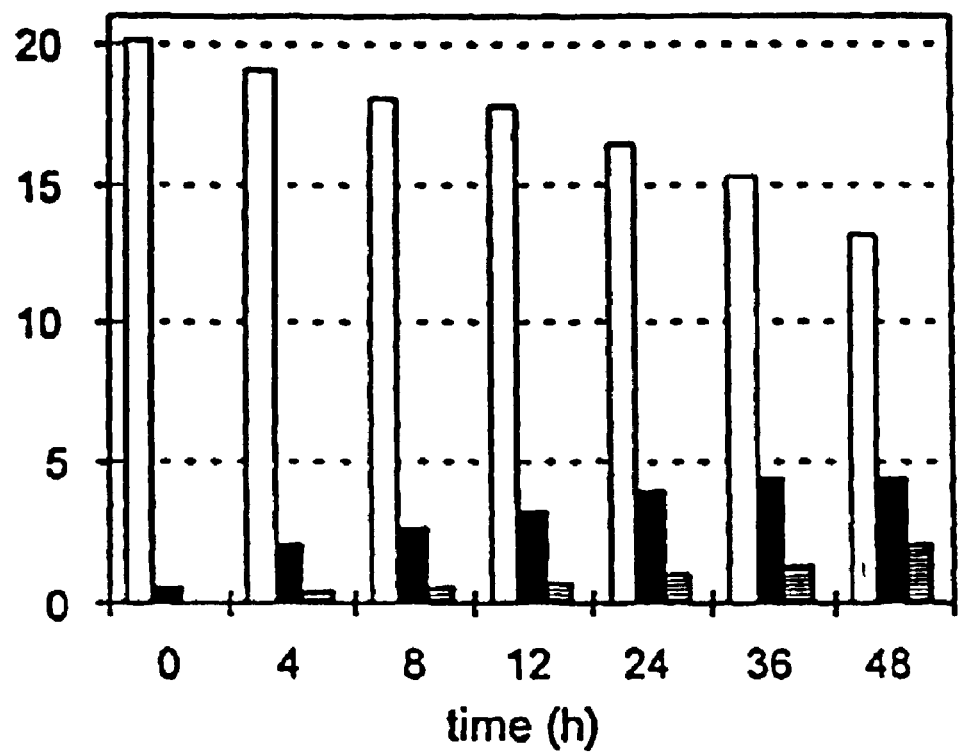
FIG. 3 is a graph showing the equilibration of shikimic and quinic acids catalyzed by SP1.1/pKD12.112.

Quinic acid formation was further explored by collecting SP1.1/pKD12.112 cells from the fermentor after 24 h. Washed cells were resuspended in fresh fermentation medium containing shikimic acid and shaken. As shown in FIG. 3, formation of quinic acid (solid bars) and 3-dehydroshikimate (hatched bars) along with a corresponding decrease in shikimic acid (open bars) concentration indicated that SP1.1/pKD12.112 was transporting shikimic acid into its cytosol. Brown, K. D. et al., *Biochim. Biophys. Acta* 428:550 (1976). Since both shikimate dehydrogenase and 3-dehydroquinate dehydratase catalyze reversible reactions, cytosolic shikimic acid could be converted back into 3-dehydroquinate. Shikimate dehydrogenase might then play a dual role by also catalyzing 3-dehydroquinate reduction.

Because of structural similarities between 3-dehydroshikimic and 3-dehydroquinic acids (Scheme 1), purified *E. coli* shikimate dehydrogenase was incubated with 3-dehydroquinic acid. Quinic acid formation was observed. The Michaelis constant, $K_m=1.2$ mM, and maximum velocity, $v_{max}=0.096$ mM$^{-1}$min$^{-1}$, for shikimate dehydrogenase-catalyzed reduction of 3-dehydroquinic acid to quinic acid compares with $K_m=0.11$ mM and $v_{max}=0.11$ mM$^{-1}$min$^{-1}$ for shikimate dehydrogenase-catalyzed reduction of 3-dehydroshikimic acid to shikimic acid.

II. Methods

General. For $^1$H NMR quantitation of solute concentrations, solutions were concentrated to dryness under reduced pressure, concentrated to dryness one additional time from $D_2O$, and then redissolved in $D_2O$ containing a known concentration of the sodium salt of 3-(trimethylsilyl)propionic-2,2,3,3-$d_4$ acid (TSP) purchased from Lancaster Synthesis Inc. Concentrations were determined by comparison of integrals corresponding to each compound with the integral corresponding to TSP ($\delta=0.00$ ppm) in the $^1$H NMR. All $^1$H NMR spectra were recorded on a Varian VXR-300 FT-NMR Spectrometer (300 MHz).

Culture Medium. All medium was prepared in distilled, deionized water. M9 salts (1 L) contained $Na_2HPO_4$ (6 g), $KH_2PO_4$ (3 g), NaCl (0.5 g) and $NH_4Cl$ (1 g). M9 minimal medium (1 L) consisted of 1 L of M9 salts containing D-glucose (10 g), $MgSO_4$ (0.12 g), thiamine hydrochloride (0.001 g), L-phenylalanine (0.040 g), L-tyrosine (0.040 g), L-tryptophan (0.040 g), p-hydroxybenzoic acid (0.010 g), potassium p-aminobenzoate (0.010 g), and 2,3-dihydroxybenzoic acid (0.010 g). Ampicillin was added (0.05 g/L) where indicated. Solutions of M9 salts, $MgSO_4$, and glucose were autoclaved individually and then mixed. Aromatic amino acids, aromatic vitamins, and ampicillin were sterilized through 0.22-μm membranes.

Fermentation medium (1 L) contained $K_2HPO_4$ (7.5 g), ammonium iron (III) citrate (0.3 g), citric acid monohydrate (2.1 g), L-phenylalanine (0.7 g), L-tyrosine (0.7 g), L-tryptophan (0.35 g), and concentrated $H_2SO_4$ (1.2 mL). Fermentation medium was adjusted to pH 7.0 by addition of concentrated $NH_4OH$ before autoclaving. The following supplements were added immediately prior to initiation of the fermentation: D-glucose (20 or 23 g), $MgSO_4$ (0.24 g), p-hydroxybenzoic acid (0.010 g), potassium p-aminobenzoate (0.010 g), 2,3-dihydroxybenzoic acid (0.010 g), and trace minerals including $(NH_4)_6(Mo_7O_{24})$ 5.4$H_2O$ (0.0037 g), $ZnSO_4.7H_2O$ (0.0029 g), $H_3BO_3$ (0.0247 g), $CuSO_4.5H_2O$ (0.0025 g), and $MnCl_2.4H_2O$ (0.0158 g). D-Glucose and $MgSO_4$ were autoclaved separately while aromatic vitamins and trace minerals were sterilized through 0.22-μm membranes.

Fermentations. Fermentations employed a 2.0 L working capacity B. Braun M2 culture vessel. Utilities were supplied by a B. Braun Biostat MD that was controlled by a DCU-1. Data acquisition utilized a Dell Optiplex Gs$^+$ 5166M personal computer equipped with B. Braun MFCS/Win software. Temperature, pH, and glucose feeding were controlled with PID control loops. Temperature was maintained at 33° C. pH was maintained at 7.0 by addition of concentrated $NH_4OH$ or 2 N $H_2SO_4$. Dissolved oxygen (D.O.) was measured using a Mettler-Toledo 12 mm sterilizable $O_2$ sensor fitted with an Ingold A-type $O_2$ permeable membrane. D.O. was maintained at 10% air saturation.

Inoculants were started by introduction of a single colony into 5 mL of M9 medium containing ampicillin. The culture was grown at 37° C. with agitation at 250 rpm for 24 h and subsequently transferred to 100 mL of M9 medium containing ampicillin. After growth at 37° C., 250 rpm for an additional 12 h, the inoculant was ready for transfer into the fermentation vessel. The initial glucose concentration in the fermentation medium was 20 g/L for SP1.1/pKD12.112 runs and 23 g/L for QP1.1/pKD12.112 runs. Three staged methods were used to maintain D.O. levels at 10% air saturation during the course of run. With the airflow at an initial setting of 0.06 L/L/min, D.O. concentration was maintained by increasing the impeller speed from its initial set point of 50 rpm to its preset maximum of 940 rpm. With the impeller constant at 940 rpm, the mass flow controller then maintained D.O. levels by increasing the airflow rate from 0.06 L/L/min to a preset maximum of 1.0 L/L/min. At constant impeller speed and constant airflow rate, D.O. levels were finally maintained at 10% air saturation for the remainder of the fermentation by oxygen sensor-controlled glucose feeding. At the beginning of this stage, D.O. levels fell below 10% air saturation due to residual initial glucose in the medium. This lasted for approximately 1 h before glucose (65% w/v) feeding started. The PID control parameters were set to 0.0 (off) for the derivative control ($\tau_D$) and 999.9 s (minimum control action) for integral control ($\tau_1$). $X_p$ was set to 950% to achieve a $K_c$ of 0.1.

Samples (10 mL) of fermentation broth were taken at 6 h intervals. Cell densities were determined by dilution of fermentation broth with water (1:100) followed by measurement of absorption at 600 nm ($OD_{600}$). Dry cell weight (g/L) was obtained using a conversion coefficient of 0.43 g/L/$OD_{600}$. The remaining fermentation broth was centrifuged for 4 min using a Beckman microcentrifuge to obtain cell-free broth. Solute concentrations in the cell-free broth were determined by $^1$H NMR.

SPECIFIC EXAMPLE 2

Synthesis of Quinic Acid from Glucose

I. Results

Microbes were cultured under fed-batch fermentor conditions at 33° C., pH 7.0, with dissolved oxygen maintained at a set point of 10% air saturation. D-Glucose addition was controlled by dissolved $O_2$ concentration and was a critical control parameter during syntheses of shikimic and quinic acids. When dissolved oxygen levels exceeded the set point value indicating decreased microbial metabolism, the rate of D-glucose addition was increased. When dissolved oxygen levels declined below the set point value indicating increased microbial metabolism, the rate of D-glucose addition was decreased. Proportional-integral-derivative control (PID) was used to control the rate of D-glucose addition.

QP1.1/pKD12.112 was cultured for 60 h under fed-batch fermentor conditions at 37° C., pH 7.0, dissolved oxygen at 10% of saturation and an initial glucose concentration of 23 g/L. Extracellular accumulation of quinic acid began in early to mid log phase of microbial growth as represented by the open boxes in FIG. 2. The dry cell weight is represented by the solid line and closed circles. 3-Dehydroquinate was efficiently converted to quinic acid as there was never a build-up of the intermediate (solid bars in FIG. 2). After 60 hours of cultivation with $K_c=0.1$, $E.$ $Coli$ QP1.1/pKD12.112 synthesized 60 g/L of quinic acid in 23% yield along with only 2.6 g of 3-dehydroquinate. Quinic acid was isolated from the fermentation broth by ion-exchange chromatography on AG1-x8 (acetate form) and Dowex 50 (H+ form) columns. Purified quinic acid was obtained by further recrystallization.

Figure 2:
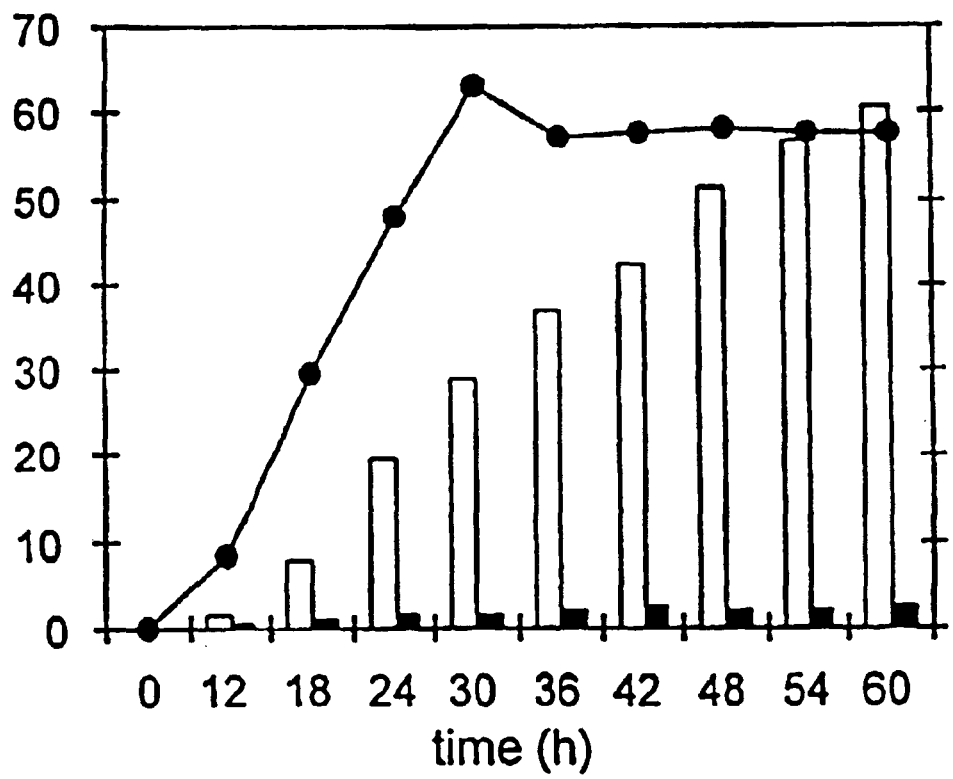
FIG. 2 is a graph showing the production of quinic acid in comparison to cell dry weight.

The yields of quinic acid obtained from culturing of the homologous construct QP1.1/pKD12.112 were significantly greater than those reported for the heterologous construct $E.$ $coli$ AB2848aroD/pKD136/pTW8090A. Cultures of QP1.1/pKD12.112 produced approximately 20 g/L of quinic acid after 24 hours and 60 g/L after 60 hours (FIG. 2). In contrast, $E.$ $coli$ AB2848aroD/pKD136/pTW8090A only produced 10.7 g/L of quinic acid after 24 hours. U.S. Pat. No. 5,798,236; Draths, K. M. et al., *J. Am. Chem. Soc.* 114:9725 (1992).

Microbial synthesis of quinic acid may supplant isolation of this hydroaromatic from plant sources which has limited its synthetic utility. At the same time, increased availability of quinic acid may portend wider utilization of this hydroaromatic. The theoretical maximum yield of microbial synthesis of quinic acid is 43% from D-glucose. Draths, K. M. et al., *J. Am. Chem. Soc.* 117:2395 (1995). Comparison with the yields achieved thus far for microbial synthesis of quinic acid (23%) along with the apparent lack of toxicity of this hydroaromatic towards the microbial biocatalyst, suggest that sizable increases in yields and titers are possible.

II. Methods

General. For $^1$H NMR quantitation of solute concentrations, solutions were concentrated to dryness under reduced pressure, concentrated to dryness one additional time from $D_2O$, and then redissolved in $D_2O$ containing a known concentration of the sodium salt of 3-(trimethylsilyl)propionic-2,2,3,3-$d_4$ acid (TSP) purchased from Lancaster Synthesis Inc. Concentrations were determined by comparison of integrals corresponding to each compound with the integral corresponding to TSP ($\delta=0.00$ ppm) in the $^1$H NMR. All $^1$H NMR spectra were recorded on a Varian VXR-300 FT-NMR Spectrometer (300 MHz).

Culture Medium. All medium was prepared in distilled, deionized water. M9 salts (1 L) contained $Na_2HPO_4$ (6 g), $KH_2PO_4$ (3 g), NaCl (0.5 g) and $NH_4Cl$ (1 g). M9 minimal medium (1 L) consisted of 1 L of M9 salts containing D-glucose (10 g), $MgSO_4$ (0.12 g), thiamine hydrochloride (0.001 g), L-phenylalanine (0.040 g), L-tyrosine (0.040 g), L-tryptophan (0.040 g), p-hydroxybenzoic acid (0.010 g), potassium p-aminobenzoate (0.010 g), and 2,3-dihydroxybenzoic acid (0.010 g). Ampicillin was added (0.05 g/L) where indicated. Solutions of M9 salts, $MgSO_4$, and glucose were autoclaved individually and then mixed. Aromatic amino acids, aromatic vitamins, and ampicillin were sterilized through 0.22-$\mu$m membranes.

Fermentation medium (1 L) contained $K_2HPO_4$ (7.5 g), ammonium iron (III) citrate (0.3 g), citric acid monohydrate (2.1 g), L-phenylalanine (0.7 g), L-tyrosine (0.7 g), L-tryptophan (0.35 g), and concentrated $H_2SO_4$ (1.2 mL). Fermentation medium was adjusted to pH 7.0 by addition of concentrated $NH_4OH$ before autoclaving. The following supplements were added immediately prior to initiation of the fermentation: D-glucose (23 g), $MgSO_4$ (0.24 g), p-hydroxybenzoic acid (0.010 g), potassium p-aminobenzoate (0.010 g), 2,3-dihydroxybenzoic acid (0.010 g), and trace minerals including $(NH_4)_6(Mo_7O_{24}) \cdot 4H_2O$ (0.0037 g), $ZnSO_4 \cdot 7H_2O$ (0.0029 g), $H_3BO_3$ (0.0247 g), $CuSO_4 \cdot 5H_2O$ (0.0025 g), and $MnCl_2 \cdot 4H_2O$ (0.0158 g). D-Glucose and $MgSO_4$ were autoclaved separately while aromatic vitamins and trace minerals were sterilized through 0.22-$\mu$m membranes.

Fermentation. Fermentation employed a 2.0 L working capacity B. Braun M2 culture vessel. Utilities were supplied by a B. Braun Biostat MD that was controlled by a DCU-1. Data acquisition utilized a Dell Optiplex Gs+ 5166M personal computer equipped with B. Braun MFCS/Win software. Temperature, pH, and glucose feeding were controlled with PID control loops. Temperature was maintained at 33° C. pH was maintained at 7.0 by addition of concentrated $NH_4OH$ or 2 N $H_2SO_4$. Dissolved oxygen (D.O.) was measured using a Mettler-Toledo 12 mm sterilizable $O_2$ sensor fitted with an Ingold A-type $O_2$ permeable membrane. D.O. was maintained at 10% air saturation.

An inoculant was started by introduction of a single colony into 5 mL of M9 medium containing ampicillin. The culture was grown at 37° C. with agitation at 250 rpm for 24 h and subsequently transferred to 100 mL of M9 medium containing ampicillin. After growth at 37° C., 250 rpm for an additional 12 h, the inoculant was ready for transfer into the fermentation vessel. The initial glucose concentration in the fermentation medium was 23 g/L. Three staged methods were used to maintain D.O. levels at 10% air saturation during the course of run. With the airflow at an initial setting of 0.06 L/L/min, D.O. concentration was maintained by increasing the impeller speed from its initial set point of 50 rpm to its preset maximum of 940 rpm. With the impeller constant at 940 rpm, the mass flow controller then maintained D.O. levels by increasing the airflow rate from 0.06 L/L/min to a preset maximum of 1.0 L/L/min. At constant impeller speed and constant airflow rate, D.O. levels were finally maintained at 10% air saturation for the remainder of the fermentation by oxygen sensor-controlled glucose feeding. At the beginning of this stage, D.O. levels fell below 10% air saturation due to residual initial glucose in the medium. This lasted for approximately 1 h before glucose (65% w/v) feeding started. The PID control parameters were set to 0.0 (off) for the derivative control ($\tau_D$) and 999.9 s (minimum control action) for integral control ($\tau_1$). $X_p$ was set to 950% to achieve a $K_c$ of 0.1.

Samples (10 mL) of fermentation broth were taken at 6 h intervals. Cell densities were determined by dilution of fermentation broth with water (1:100) followed by measurement of absorption at 600 nm ($OD_{600}$). Dry cell weight (g/L) was obtained using a conversion coefficient of 0.43 g/L/$OD_{600}$. The remaining fermentation broth was centrifuged for 4 min using a Beckman microcentrifuge to obtain cell-free broth. Solute concentrations in the cell-free broth were determined by $^1$H NMR.

Purification of Quinic Acid from Fermentation Broth. The fermentation broth (1100–1200 mL) was centrifuged at 14000 g for 20 min and the cells were discarded. The resulting supernatant was refluxed for 1 h, cooled to room temperature, and the pH adjusted to 2.5 by addition of concentrated $H_2SO_4$. After centrifugation at 14000 g for 20 min, a clear yellow solution was poured away from the cellular debris and adjusted to pH 6.9 by addition of concentrated $NH_4OH$. The solution was combined with 10 g of Darco KB-B activated carbon, swirled at 50 rpm for 1–2 h, and then filtered through Whatman 5 filter paper. Filtered material was washed with an additional 300 mL of water.

Following treatment with activated carbon, the solution was slightly gray in color. Addition of glacial acetic acid to a final concentration of 25% afforded a clear, yellow solution which was then eluted through a column of AG1-x8 (acetate form, 5 cm×20 cm) at 4° C. Following elution of the column with an additional 400 mL of 25% aqueous acetic acid, the combined eluents were passed through a column of Dowex 50 ($H^+$ form, 5 cm×20 cm) at 4° C. which was then washed with 400 mL of 25% aqueous acetic acid. The eluents off the cation exchange column were combined and were concentrated to dryness by rotary evaporation, leaving a hard white solid (80% recovery through this step). Recrystallization from ethanol afforded a fine, white powder (52% recovery based on quinic acid quantified in crude fermentation broth).

SPECIFIC EXAMPLE 3

Synthesis of Hydroquinone from Quinic Acid with Acidified NaOCl

I. Results

Figure 5:
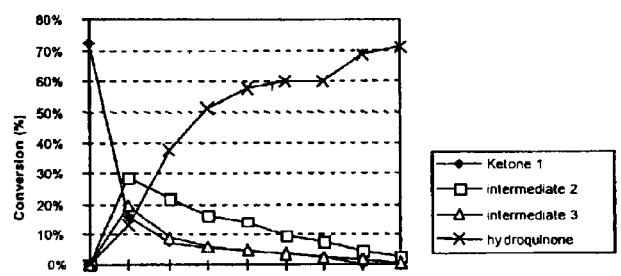
FIG. 5 is a graph showing the production of hydroquinone over time with relation to synthetic intermediates.

Hydroquinone was synthesized from quinic acid as shown in the synthetic scheme of FIG. 4. Quinic acid was oxidized to 3(R),4(S),5(R)-trihydroxycyclohexanone 1 upon reaction with acidified ($H_2SO_4$) commercial bleach (NaOCl). After quenching excess oxidant with isopropanol E, heating 1 afforded hydroquinone via intermediacy of cyclohexanones 2 and 3 (FIG. 4). The progress of the reaction upon heating with respect to time is shown in FIG. 5. As trihydroxycyclohexanone 1 (solid diamonds in FIG. 5) decreases, initial increases are observed for cyclohexanones 2 and 3 (open squares and shaded triangles, respectively, in FIG. 5). As the reaction progresses, the intermediates decrease and hydroquinone is formed (-x- in FIG. 5).

II. Methods

General Chemistry. $^1H$ NMR spectra were recorded at 300 MHz on a Varian Gemini-300 spectrometer. Chemical shifts for $^1H$ NMR spectra are reported (in parts per million) relative to internal tetramethylsilane ($Me_4Si$, δ=0.0 ppm) with $CDCl_3$ as a solvent, and to sodium 3-(trimethylsilyl) propionate-2,2,3,3-d4 (TSP, δ=0.0 ppm) when $D_2O$ was the solvent. $^{13}C$ NMR spectra were recorded at 75 MHz on a Gemini-300 spectrometer. Chemical shifts for $^{13}C$ NMR spectra are reported (in parts per million) relative to $CDCl_3$ (δ=77.0 ppm) or internal acetonitrile ($CH_3CN$, δ=3.69 ppm) in $D_2O$.

Purification of quinic acid from fermentation broth. Quinic acid was synthesized by the methods of Specific Example 2. Following removal of cells, 1 L of crude culture supernatant containing quinic acid (82.9 g, 0.431 mol, 1000 mL) was refluxed for 1 h. After the solution cooled to room temperature, concentrated sulfuric acid was added to a final pH of 2.5. The resulting solution was then centrifuged and filtered, the supernatant was decolorized by stirring with charcoal (20 g) at room temperature for 2 hours. Finally, the clear solution was passed through Dowex 50 ($H^+$) column at 4° C. to afford an aqueous quinic acid solution. (81.5 g, 0.424 mol, 98%).

Synthesis of hydroquinone. To a stirred solution of the purified quinic acid (81.5 g, 0.424 mol) in 1120 mL broth at room temperature was added commercial bleach (1800 mL) and $H_2SO_4$ (178 mL, 2 M final concentration) dropwise over a 1 h period. The mixture was stirred for an additional 2 hours. Isopropanol (130 mL) was added to quench unreacted HOCl. The resulting solution which contained 3(R),4(S),5(R)-trihydroxycyclohexanone 1 (50.1 g, 0.343 mol, 81%) was heated to reflux under an argon atmosphere for 10 h. After cooling to room temperature, hydroquinone was extracted into t-butyl methyl ether (4×500 mL) and the combined organic layers were dried over $MgSO_4$. Charcoal (20 g) was added to the solution which was then stirred for 10 minutes and subsequently filtered through Celite. The filtered residue was washed with t-butyl methyl ether (200 mL). The filtrates were concentrated in vacuo to obtain hydroquinone as a brown solid in 77% yield. Sublimation of the isolated material yielded hydroquinone as white solid in 93% yield. The overall yield from quinic acid is 57%.

Synthesis of 3(R),4(S),5(R)-trihydroxycyclohexanone (1). To a stirred solution of quinic acid (20 g, 0.104 mol) in 120 mL water at room temperature was added commercial bleach (NaOCl, 442 g) and $H_2SO_4$ (41.6 mL, 2 M final concentration). After the mixture was stirred for 3 hours, isopropanol (15.9 mL) was added and the solution was stirred for an additional 30 minutes. The resulting solution was neutralized and concentrated, and EtOH/EtOAc (300 mL, 1:1, v/v) was added to the resulting slurry and the mixture was stirred for 30 minutes. Resulting inorganic salts were removed by filtration and the resulting solution was concentrated to dryness and compound 1 was obtained as a white solid after being purified by flash chromatography (6.15 g, 41%). $^1H$ NMR ($D_2O$) δ 4.27–4.31 (m, 1H), 4.15 (ddd, J=8.2, 8.2, 5.1 Hz, 1H), 3.97 (dd, J=7.5, 2.7 Hz, 1H), 2.75–2.83 (m, 2H), 2.50–2.65 (m, 2H); $^{13}C$ NMR ($D_2O$) δ 215.5, 75.7, 71.4, 48.4, 48.3.

Figure 6:
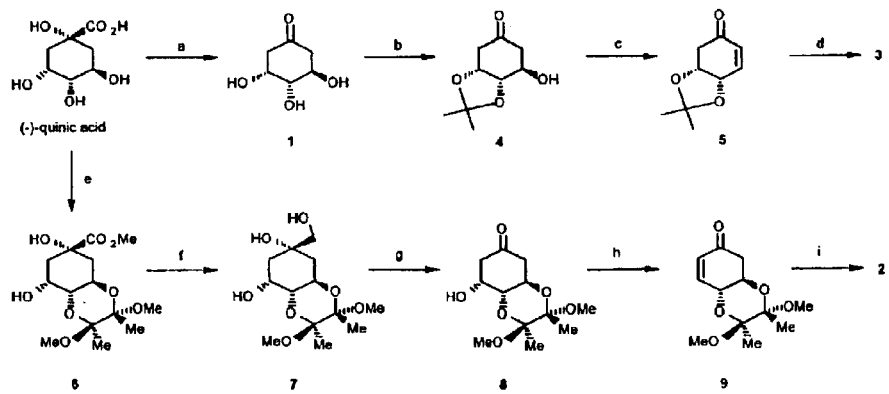
FIG. 6 is a schematic illustrating the synthesis scheme for establishing the synthetic route and relevant intermediates.

Synthesis of 3,4-O-Isopropylidene-3(R),4(S),5(R)-trihydroxycylohexanone (4). Trihydroxycyclohexanone 1 (3.0 g, 20.5 mmol) was dissolved in 60 mL acetone, and TsOH (30 mg, 0.158 mmol) was added. The solution was stirred vigorously under an argon atmosphere at room temperature for 9 hours. Removal of the solvent afforded a yellow oil which was purified by flash chromatography. Compound 4 (FIG. 6) was obtained as white crystals (2.24 g, 59%). $^1H$ NMR ($CDCl_3$) δ 4.70–4.74 (m, 1H), 4.32 (ddd, J=7.2, 2.1, 2.1 Hz, 1H), 4.24 (dd, J=6.3, 2.7 Hz, 1H), 2.82 (dd, J=17.8, 3.9 Hz, 1H), 2.70–2.72 (m, 1H), 2.65–2.66 (m, 1H), 2.46 (dm, 1H, J=17.8 Hz), 2.24 (b, 1H), 1.45 (s, 3H), 1.37 (s, 3H); $^{13}C$ NMR ($CDCl_3$) δ 208.0, 108.8, 74.9, 72.2, 68.2, 41.6, 40.1, 26.4, 23.8.

Synthesis of 3,4-O-Isopropylidene-4(S),5(R)-dihydroxy-2-cyclohexen-1-one (5). To a solution of 4 (2.0 g, 10.8 mmol) in $CH_2Cl_2$ (8 ml) at 0° C. was added 4-(dimethylamino) pyridine (20 mg), diisopropylethylamine (3.75 mL, 21.5 mmol) and acetic anhydride (1.22 mL, 12.9 mmol). After stirring for 3 hours at 0° C., the reaction mixture was washed with saturated aqueous $NaHCO_3$ (2520 ml), and the $NaHCO_3$ solution was extracted with $CH_2Cl_2$ (4×40 mL). The organic layer was dried over $MgSO_4$ and concentrated to dryness to afford a pale yellow solid. Kugelrohr distillation gave compound 5 (FIG. 6) (1.65 g, 91%) as a colorless oil which crystallized as white solid. $^1H$ NMR ($CDCl_3$) δ 6.65 (dd, J=10.2, 3.6 Hz, 1H), 6.04 (d, J=10.2 Hz, 1H), 4.71 (m, 2H), 2.93 (dd, J=17.7, 2.7 Hz, 1H), 2.70 (dd, J=17.7, 3.9 Hz, 1H), 1.39 (s, 3H), 1.38 (s, 3H); $^{13}C$ NMR ($CDCl_3$) δ 208.4; 108.7; 74.8; 72.2; 68.0; 41.5; 40.1; 26.3; 23.8.

Synthesis of 4(S),5(R)-dihydroxy-2-cyclohexen-1-one (3). Compound 5 (0.5 g, 2.98 mmol) was dissolved in $CF_3CO_2H/H_2O$ (2:1, v/v, 25 mL) and the mixture was stirred at 0° C. for 20 minutes. The solvent was removed in vacuo, and the compound was purified by flash chromatograph to give compound 3 (FIG. 6) (0.16 g, 43%) as colorless oil, which crystallized into white solid. $^1$H NMR (D$_2$O) δ 6.97 (dm, J=10.2 Hz, 1H), 6.11 (dm, J=10.2 Hz, 1H), 4.69–4.72 (m, 1H), 4.39–4.41 (m, 1H), 2.82 (ddd, J=17.0, 3.3, 0.8 Hz, 1H), 2.72 (dd, J=17.0, 5.0 Hz, 1H); $^{13}$C NMR (D$_2$O) δ 204.4; 154.2; 151.5; 72.4; 70.3; 45.6.

Synthesis of compound 7. BBA-protected methyl quinate 6 (FIG. 6) (4.0 g, 12.5 mmol) was dissolved in 50 mL dry THF at 0° C. and LiAlH$_4$ (1.42 g, 37.5 mmol) was added portionwise. The mixture was stirred for 1 hour at 0° C. then warmed to room temperature. After 10 hours, all the starting material has been consumed. The resulting mixture was cooled to 0° C. and excess hydride was quenched by careful, successive addition of water (1.4 mL), 15% aqueous NaOH (1.4 mL) and water (4.2 mL). Celite (8.0 g) was added and the slurry was stirred for 2 hours. The alumina salt was separated by vacuum filtering through a pad of Celite, and washed with hot ethyl acetate (100 mL). The filtrate was then concentrated to dryness and purified by flash chromatography to afford the desired product 7 (FIG. 6) as a white foam (3.4 g, 93%). $^1$H NMR (CDCl$_3$) δ 4.26–4.35 (m, 1H), 4.21–4.22 (m, 1H), 3.55 (dd, J=10.2, 2.7 Hz, 1H), 3.40 (dd, J=33.2, 11.0 Hz, 1H), 3.27 (s, 3H), 3.25 (s, 3H), 3.13 (b, 1H), 2.44 (b, 1H), 2.24 (dm, J=14.7 Hz, 1H), 1.93–1.98 (m, 1H), 1.38–1.52 (m, 2H), 1.33 (s, 3H), 1.30 (s, 3H); $^{13}$C NMR (CDCl$_3$) δ 100.3, 99.7, 74.1, 73.4, 70.4, 69.5, 62.9, 48.0, 47.9, 37.7, 36.0, 17.9, 17.6.

Synthesis of BBA-protected 3,4,5-trihydroxycyclohexanone (8). Triol 7 (FIG. 6) (2.5 g, 8.56 mmol) was dissolved in 50 mL phosphate buffer (pH 7) and the solution cooled to 0° C. Sodium periodate (2.74 g, 12.8 mmol) was added in portions. After the addition, the ice-bath was removed and the mixture was stirred at room temperature for 1 hour. The aqueous mixture was then extracted with ethyl acetate (4×50 mL), and the combined organic phase was dried with MgSO$_4$ and filtered through Celite. The solvent was removed in vacuo and compound 8 (FIG. 6) was obtained as a white powder. (1.61 g, 72%). $^1$H NMR (CDCl$_3$) δ 4.23–4.33 (m, 2H), 3.89 (dd, J=10.2, 2.4 Hz, 1H), 3.31 (s, 3H), 3.24 (s, 3H), 2.61–2.69 (m, 2H), 2.45–2.54 (m, 2H), 1.82 (b, 1H), 1.35 (s, 3H), 1.31 (s, 3H); $^{13}$C NMR (CDCl$_3$) δ 205.5, 100.1; 99.2; 72.2; 67.6; 63.2; 48.1; 47.9; 46.2; 44.7; 17.7; 17.5.

Synthesis of BBA-protected dihydroxycyclohexenone (9). To a solution of the β-hydroxy ketone 8 (FIG. 6) (1.01 g, 3.85 mmol) in CH$_2$Cl$_2$ (10 mL) at 0° C. was added 4-(dimethylamino) pyridine (9.4 mg, 0.077 mmol), diisopropylethylamine (1.34 mL, 7.7 mmol) and acetic anhydride (0.44 mL, 4.6 mmol). After stirring at 0° C. for 6 hours, the solution was washed with saturated aqueous NaHCO$_3$ and the NaHCO$_3$ wash solution was extracted with CH$_2$Cl$_2$ (4×40 ml). The organic layer was dried with MgSO$_4$ and concentrated to dryness. Purification by flash chromatography afforded compound 9 (FIG. 6) as a white solid (0.94 g, 100%). $^1$H NMR (CDCl$_3$) δ 6.87 (dd, J=10.2, 1.8 Hz, 1H), 6.01 (dd, J=10.2, 2.4 Hz, 1H), 4.51 (dt, J=9.0, 2.1 Hz, 1H), 4.05 (m, 1H), 3.33 (s, 3H), 3.27 (s, 3H), 2.74 (dd, J=16.5, 13.2 Hz, 1H), 1.37 (s, 3H), 1.34 (s, 3H); $^{13}$C NMR (CDCl$_3$) δ 196.8; 148.5; 130.1; 100.8; 99.7; 69.2; 8.0; 48.2; 48.1; 42.0; 17.7; 17.6.

Synthesis of 4(S),5(S)-dihydroxy-2-cyclohexen-1-one (2). The α,β-unsaturated ketone 9 (FIG. 6) (0.344 g, 1.42 mmol) was stirred in a mixture of trifluroacetic acid (18 mL), CH$_2$Cl$_2$ (2 mL) and water (2 mL) for 30 minutes at 0° C. Solvents were removed in vacuo. The residue was azotroped with toluene (20 ml) and purified by flash chromatography to give compound 2 (FIG. 4) as a white solid (0.137 g, 75%). $^1$H NMR (D$_2$O) δ 7.04 (dd, J=10.2, 2.4 Hz, 1H), 6.08 (dm, J=10.2 Hz, 1H), 4.45 (dm, J=8.4 Hz, 1H), 3.99–4.07 (m, 1H), 2.82 (ddd, J=16.4, 4.8, 1.2 Hz, 1H), 2.58 (dd, J=16.4, 11.9 Hz, 1H); $^{13}$C NMR (D$_2$O) δ 204.8, 156.1, 131.4, 74.4, 74.3, 46.5.

SPECIFIC EXAMPLE 4

Synthesis of Hydroquinone from Quinic Acid with AgNO$_3$

To quinic acid broth (106 mL containing 1.84 g, 9.6 mmol quinic acid), K$_2$S$_2$O$_8$ (3.11 g, 11.5 mmol) and AgNO$_3$ (0.163 g, 0.96 mmol) was added. The solution was stirred vigorously at 50° C. under an argon atmosphere for 4 h and then heated to reflux for an additional 9 h. Extraction with ethyl acetate (4×50 mL) followed by drying over MgSO$_4$ and concentration afforded a brown solid. Purification by flash chromatography yielded hydroquinone (0.37 g, 35%) as a white solid.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All references cited herein are incorporated by reference as if fully set forth. In addition, U.S. Ser. No. 09/240,440, entitled "Biocatalytic Synthesis Of Shikimic Acid," filed Jan. 29, 1999, is also expressly incorporated by reference.

What is claimed is:

1. A method for the production of 3,4,5-trihydroxycyclohexanone from quinic acid, comprising: oxidizing the quinic acid to 3,4,5-trihydroxycyclohexanone with an oxidizing agent selected from the group consisting of HOCL, AgNO$_3$, (NH$_4$)$_2$Ce(NO$_3$)$_6$, V$_2$O$_5$, NH$_4$VO$_3$, and 2KHSO$_5$.KHSO$_4$.K$_2$SO$_4$/NaCl.

2. The method of claim 1, wherein the oxidizing agent is HOCl.

3. The method of claim 1, wherein the oxidizing agent is AgNO$_3$.

4. The method of claim 1, wherein the oxidizing agent is AgNO$_3$ and K$_2$S$_2$O$_8$ is a cooxidant.

5. The method of claim 1, wherein the oxidizing agent is (NH$_4$)$_2$Ce(NO$_3$)$_6$.

6. The method of claim 1, wherein the oxidizing agent is V$_2$O$_5$.

7. The method of claim 1, wherein the oxidizing agent is NH$_4$VO$_3$.

8. The method of claim 1, wherein the oxidizing agent is 2KHSO$_5$.KHSO$_4$.K$_2$SO$_4$/NaCl.

9. The method of claim 1, wherein the quinic acid is produced by a recombinant microbe.

10. The method of claim 2, wherein the oxidizing agent is HOCl obtained by acidifying NaOCl.

11. The method of claim 1, wherein the oxidizing the quinic acid further comprises reacting the quinic acid with a cooxidant.

12. A method for the production of hydroquinone from 3,4,5-trihydroxycyclohexanone, comprising: dehydrating 3,4,5-trihydroxycyclohexanone to produce hydroquinone, wherein said 3,4,5-trihydroxycyclohexanone is prepared by oxidizing quinic acid to 3,4,5-trihydroxycyclohexanone with an oxidizing agent selected from the group consisting of HOCL, AgNO$_3$, (NH$_4$)$_2$Ce(NO$_3$)$_6$, V$_2$O$_5$, NH$_4$VO$_3$, and 2KHSO$_5$.KHSO$_4$.K$_2$SO$_4$/NaCl.

13. The method of claim 12, wherein the quinic acid is produced by a recombinant microbe.

* * * * *

UNITED STATES PATENT AND TRADEMARK OFFICE
CERTIFICATE OF CORRECTION

PATENT NO. : 7,002,047 B2  Page 1 of 1
APPLICATION NO. : 10/435242
DATED : February 21, 2006
INVENTOR(S) : John W. Frost and Karen M. Frost It is certified that error appears in the above-identified patent and that said Letters Patent is hereby corrected as shown below:

Column 4, line 56, "shildmate" should be --shikimate--.

Column 5, line 22, "dehydroshikimate" should be --shikimate--.

Column 14, line 33, Claim 1, "HOCL" should be --HOCl--.

Column 14, line 61, Claim 12, "HOCL" should be --HOCl--.

Signed and Sealed this

Twenty-eighth Day of November, 2006

JON W. DUDAS
*Director of the United States Patent and Trademark Office*

UNITED STATES PATENT AND TRADEMARK OFFICE
CERTIFICATE OF CORRECTION

PATENT NO. : 7,002,047 B2
APPLICATION NO. : 10/435242
DATED : February 21, 2006
INVENTOR(S) : John W. Frost et al.

It is certified that error appears in the above-identified patent and that said Letters Patent is hereby corrected as shown below:

In the Specification:
Column 1 Line 12 delete:

"SPONSORSHIP

Work on this invention was sponsored in part by the United States Department Of Agriculture Grant No. 95-37500-1930 and the National Science Foundation Grant No. CHE963368 amendment 002. The Government may have certain rights in the invention."

and insert therefor:

--GOVERNMENT LICENSE RIGHTS

This invention was made with government support under CHE9633368 awarded by the National Science Foundation and under 95-37500-1930 awarded by the U.S. Department of Agriculture. The government has certain rights in the invention.--

Signed and Sealed this
Ninth Day of June, 2015

Michelle K. Lee
*Director of the United States Patent and Trademark Office*